(12) United States Patent
Van Der Spek et al.

(10) Patent No.: US 10,394,207 B2
(45) Date of Patent: Aug. 27, 2019

(54) TECHNIQUES FOR OPTIMIZING PERFORMANCE OF CYCLONES

(71) Applicant: CiDRA Corporate Services Inc., Wallingford, CT (US)

(72) Inventors: Alex M. Van Der Spek, Rotterdam (NL); Americo J. Zuzunaga, New Haven, CT (US); Jerin J. Russell, Ellington, CT (US); Robert J. Maron, Middletown, CT (US)

(73) Assignee: CiDRA Corporate Service Inc., Wallingford, CT (US)

( * ) Notice: Subject to any disclaimer, the term of this patent is extended or adjusted under 35 U.S.C. 154(b) by 409 days.

(21) Appl. No.: 14/914,048

(22) PCT Filed: Aug. 26, 2014

(86) PCT No.: PCT/US2014/052628
§ 371 (c)(1),
(2) Date: Feb. 24, 2016

(87) PCT Pub. No.: WO2015/031308
PCT Pub. Date: Mar. 5, 2015

(65) Prior Publication Data
US 2016/0207050 A1 Jul. 21, 2016

Related U.S. Application Data

(60) Provisional application No. 61/869,901, filed on Aug. 26, 2013.

(51) Int. Cl.
*B04C 5/24* (2006.01)
*B04C 11/00* (2006.01)
(Continued)

(52) U.S. Cl.
CPC .............. *G05B 19/042* (2013.01); *B04C 5/24* (2013.01); *B04C 11/00* (2013.01); *B25B 11/00* (2013.01);
(Continued)

(58) Field of Classification Search
USPC ....................................................... 700/286
See application file for complete search history.

(56) References Cited

U.S. PATENT DOCUMENTS 3,596,839 A 8/1971 Putman
5,132,024 A 7/1992 Hulbert
(Continued)

FOREIGN PATENT DOCUMENTS

WO 2011130783 A1 10/2011

OTHER PUBLICATIONS

Grace J. R., Cui, H. And Elnashaie, S., "Non-uniform Distribution of Two-Phase flows through parallel identical paths," The Candaian Journal of Chemical Engineering, vol. 85, Oct. 2007, pp. 662-668.*
(Continued)

*Primary Examiner* — Roy Y Yi
(74) *Attorney, Agent, or Firm* — Ware, Fressola, Maguire & Barber LLP

(57) ABSTRACT

Apparatus is provided including a signal processor or signal processing module configured at least to: respond to signaling containing information about particle sizes of solids forming part of a slurry stream being fed with a common feed flow into a battery of cyclones; and determine which combinations of cyclones in the battery produce overflow that has undesirable particle size characteristics using a statistical algorithm or technique, based upon the signaling received. The signal processor or signal processing module provides corresponding signaling containing about which combinations of cyclones in the battery produce overflow
(Continued)

that has undesirable particle size characteristics, including control signaling to control the operation of the battery, including information about certain combinations of cyclones to avoid, or preferentially to use, to minimize the total amount of coarse material having the undesirable particle size characteristics produced by the battery.

36 Claims, 8 Drawing Sheets

(51) Int. Cl.
*G01M 1/00* (2006.01)
*G01M 13/00* (2019.01)
*G01N 15/02* (2006.01)
*G05B 19/042* (2006.01)
*B25B 11/00* (2006.01)

(52) U.S. Cl.
CPC .............. *G01M 1/00* (2013.01); *G01M 13/00* (2013.01); *G01N 15/02* (2013.01); *G05B 2219/2639* (2013.01)

(56) References Cited

U.S. PATENT DOCUMENTS

| | | |
|---|---|---|
| 6,082,934 A | 7/2000 | Reinsch et al. |
| 6,269,952 B1 * | 8/2001 | Watt .................. B01J 19/10 209/17 |
| 7,134,320 B2 | 11/2006 | Gysling et al. |
| 7,165,464 B2 | 1/2007 | Gysling et al. |
| 7,255,790 B2 | 8/2007 | Rogers et al. |
| 7,343,820 B2 | 3/2008 | Gysling et al. |
| 7,363,800 B2 | 4/2008 | Gysling |
| 7,367,240 B2 | 5/2008 | Gysling et al. |
| 2008/0236298 A1 | 10/2008 | Gysling |
| 2012/0209550 A1 * | 8/2012 | Van Der Spek ...... G01F 1/7082 702/63 |

OTHER PUBLICATIONS

O'Keefe, C. V., Maron, R. J., Rothman, P. J. and Poplawski, J., "Description of Non-Intrusive Sonar Array-Based Technology and its Application to Unique and Difficult Slurry and Paste Flow Measurements," May 2008 (14 pages).

Grace, J. R., Cui, H. and Elnashaie, S., "Non-Uniform Distribution of Two-Phase Flows Through parallel Identical Paths," The Canadian Journal of Chemical Engineering, vol. 85, Oct. 2007, pp. 662-668.

International Search Report dated Nov. 24, 2014 in parent international patent application No. PCT/US2014/052628 (3 pages).

Benes P., et al., "In Process Measurement of Particle Size Distribution", IEEE 2004.

Nieto L., et al., "A Virtual Sensor for Estimating Particle Size of Hydrocyclones Overflow", Oct. 2009.

Miroslav, U., et al., "Measurement of Particle Size Distribution by the Use of Acoustic Emission Method", IEEE 2012.

* cited by examiner

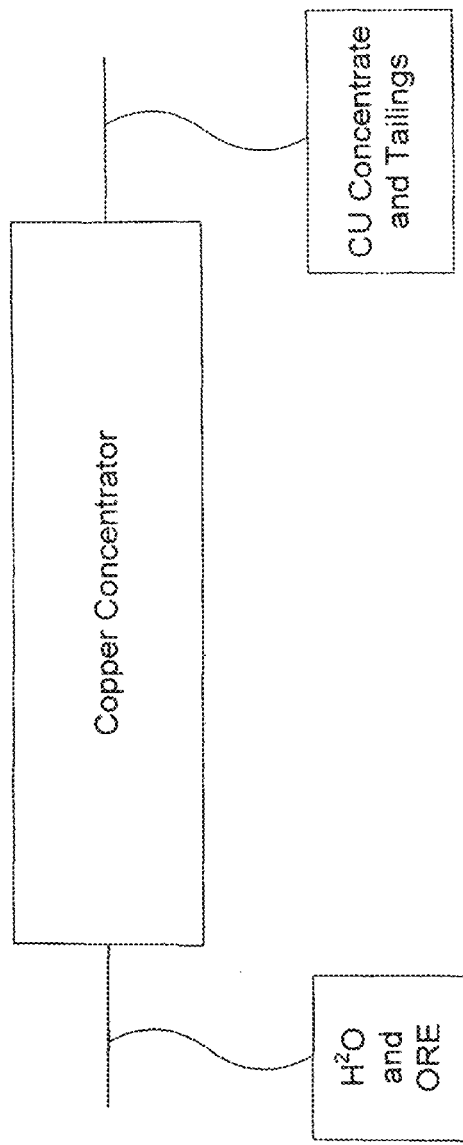
FIGURE 1A: Mineral Extraction Processing System - Prior Art

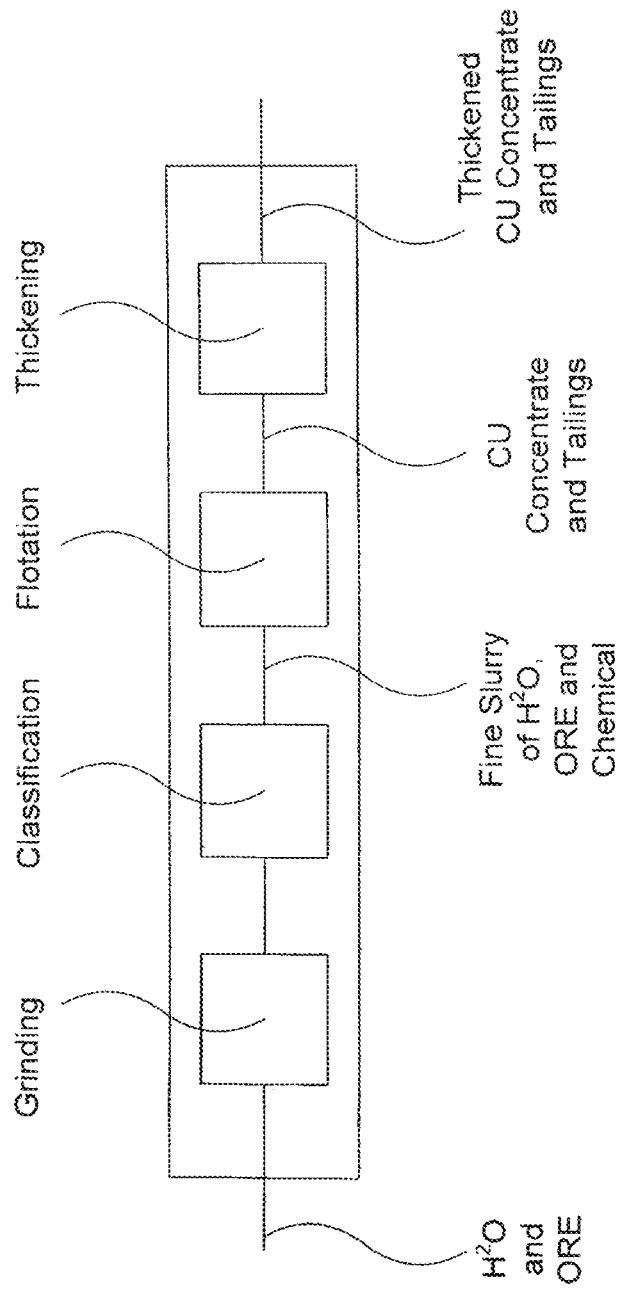
FIGURE 1B: - Prior Art

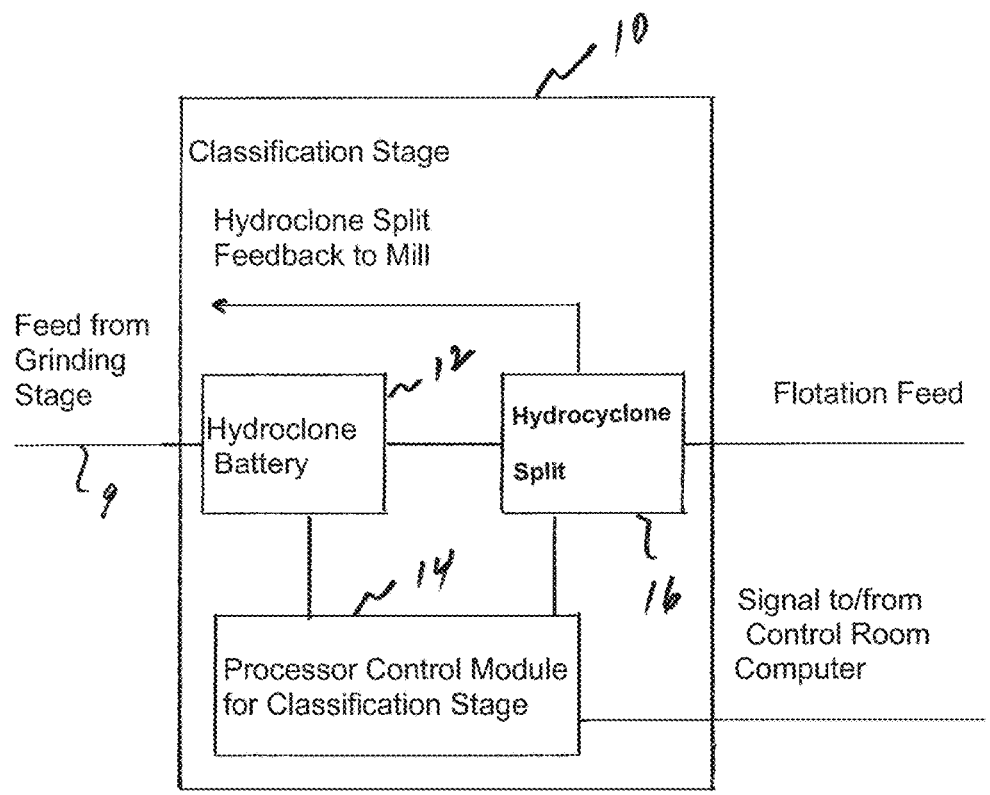
FIGURE 2: Classification Stage - Prior Art

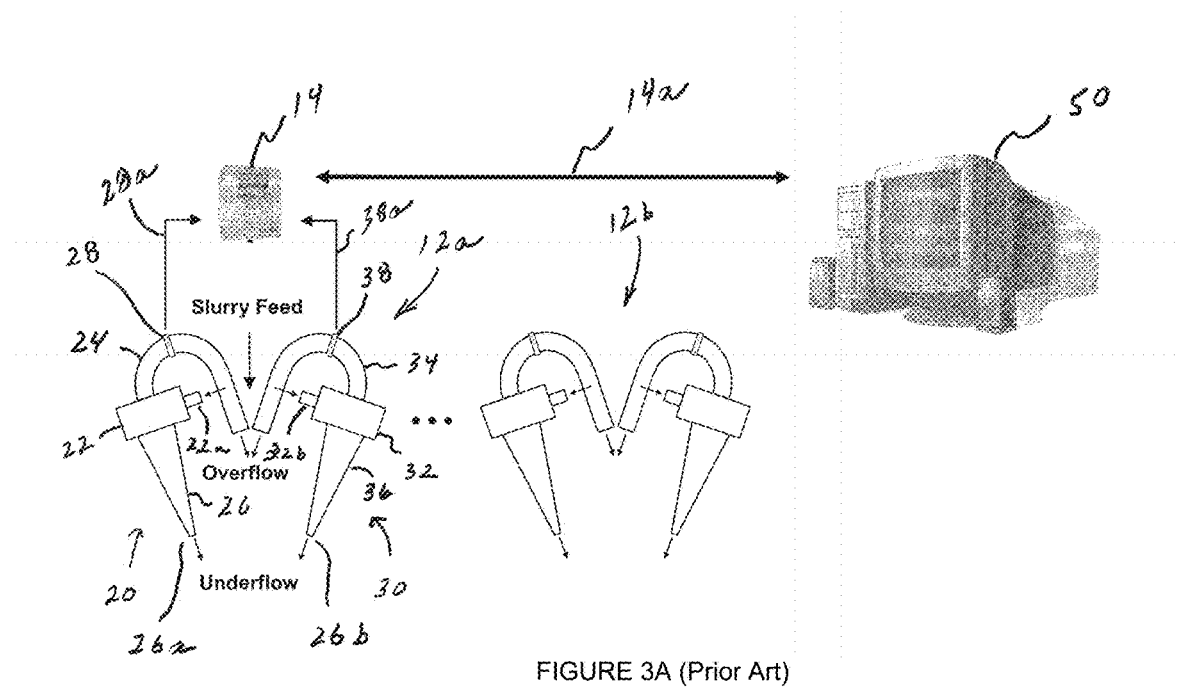
FIGURE 3A (Prior Art)
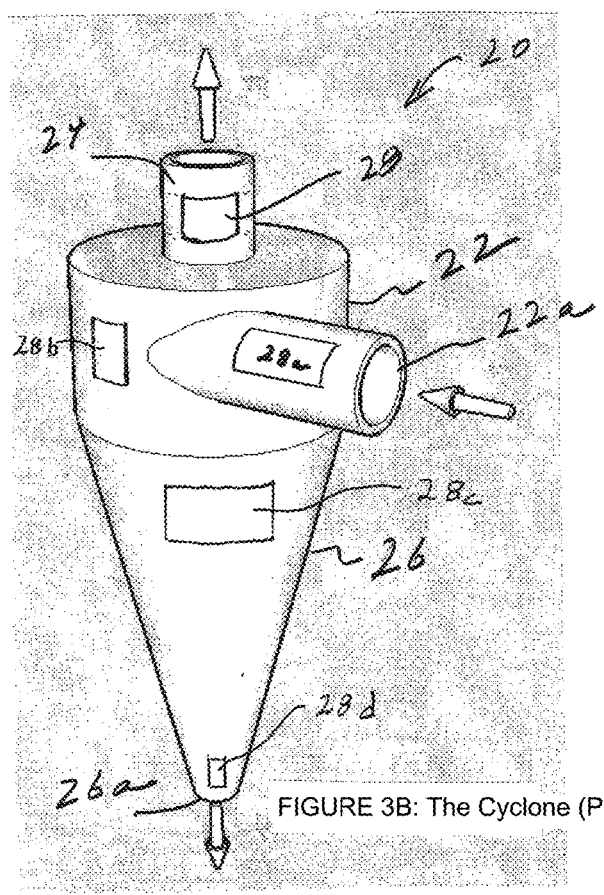
FIGURE 3B: The Cyclone (Prior Art)

FIGURE 3C: Oversize detection system on hydrocyclone overflow line (Prior Art)
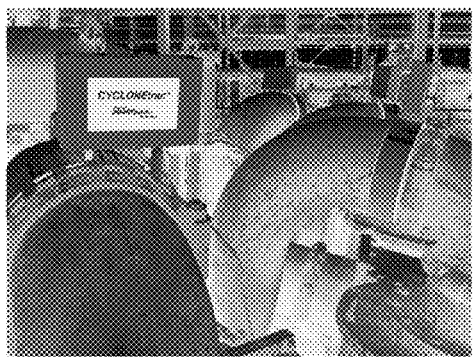

FIGURE 3D: Control room display of real-time cyclone information (Prior Art)
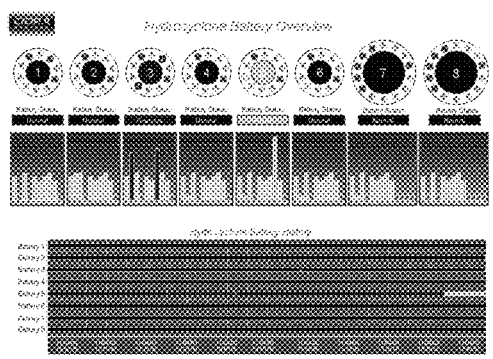

TECHNIQUES FOR OPTIMIZING PERFORMANCE OF CYCLONES

CROSS-REFERENCE TO RELATED APPLICATIONS

This applications corresponds to international patent application serial no. PCT/US2014/052628, filed 26 Aug. 2014, which claims benefit to provisional patent application Ser. No. 61/869,901 (712-2.410//CCS-0124), filed 26 Aug. 2013; which is incorporated by reference in its entirety.

This application is related to patent application Ser. No. 13/389,546 (712-2.330-1-1), which corresponds to PCT/US10/45178, filed 11 Aug. 2010, claiming benefit to provisional patent application Ser. No. 61/232,875 (CCS-0026), filed 11 Aug. 2009; Ser. No. 61/400,819 (CCS-0044), filed 2 Aug. 2010; and Ser. No. 61/370,154 (CCS-0043), filed 3 Aug. 2010, which are all incorporated by reference in their entirety.

This application is also related to patent application Ser. No. 13/377,083 (712-2.326-1-1//CCS-0027), which corresponds to PCT/US10/38281, filed 11 Jun. 2010, claiming benefit to provisional patent application Ser. No. 61/186,502, 12 Jun. 2009, which are all incorporated by reference in their entirety.

This application is related to patent application Ser. No. 12/991,636 (712-2.322-1-1//CC-0962), which corresponds to PCT/US09/43438, filed 11 May 2009, claiming benefit to provisional patent application Ser. No. 61/051,775 (CC-0962P), 61/051,781 (CCS-0963P), and 61/051,803 (CCS-0964P), all filed 9 May 2008, which are all incorporated by reference in their entirety.

The aforementioned applications were all assigned to the assignee of the present application, which builds on this family of technology.

BACKGROUND OF THE INVENTION

1. Field of Invention

This invention relates to a technique for optimizing the performance of cyclones, e.g., operating in a hydrocyclone battery in a mineral extraction processing system, including extracting a mineral from ore.

2. Description of Related Art

By way of example, the aforementioned patent application Ser. No. 13/389,546 (712-2.330-1-1//CCS-0026, 43 and 44) discloses techniques for performance monitoring of individual cyclones using a SONAR-based slurry flow measurement, e.g., consistent with that disclosed in relation to FIGS. 1A-1B, 2 and 3A-3D herein.

As disclosed in the aforementioned patent application Ser. No. 13/389,546, in many industrial processes the sorting, or classification, of product by size is critical to overall process performance. A minerals processing plant, or beneficiation plant, is no exception. In the case of a copper concentrator as shown in FIG. 1A, the input to the plant is water and ore (of a particular type and size distribution) and the outputs are copper concentrate and tailings. The process consists of a grinding, classification, floatation, and thickening, as shown in FIG. 1B. The grinding and classification stage produces a fine slurry of water and ore, to which chemicals are added prior to being sent to the flotation stage. Once in the flotation stage, air is used to float the copper mineral while the gangue (tailings) is depressed. The recovered copper is cleaned and dried. The tailings are thickened and sent to the tailings pond. The classification stage is critical to the performance of two areas of the process. These areas are the grinding throughput and flotation recovery, grade and throughput.

A grinding operation may include a screens and crusher stage and a mill stage, that is typically configured mills in closed circuit with a hydrocyclone battery. A hydrocyclone is a mechanical device that will separate a slurry stream whereby the smaller particles will exit out the overflow line and the larger particles will exit out the underflow line. The overflow is sent to the flotation circuit and the underflow is sent back to the mill for further grinding. A collection of these devices is called a battery. A hydrocyclone will be sized based on the particular process requirements. The performance of the hydrocyclone is dependent on how well it is matched to the process conditions. Once the proper hydrocyclone has been chosen and installed, it must be operated within a specific range in order to maintain the proper split between the overflow and the underflow. The split is dependent on slurry feed density and volumetric flow into the device. A typical control system will use a combination of volumetric flow, feed density and pressure across the hydrocyclone to control the split. Because of the harsh environmental and process conditions all of these measurements suffer from maintenance and performance issues. This can result in reduced classification performance and reduced mill throughput. Flotation performance is highly dependent on the particle size distribution in the feed which comes from the battery overflow, thus it is dependent on the hydrocyclone classification performance. The mill throughput is highly dependent on the circulation load which comes from the battery underflow. Traditionally hydrocyclone performance has been determined by evaluating manually collected samples from the consolidated hydrocyclone battery overflow stream. This technique is time consuming; the accuracy is subject to sampling techniques; the sample is a summation of all the hydrocyclones from the battery; and has a typical 24 hour turnaround time. Therefore it is not possible to implement a real time control algorithm to monitor, control, and optimize the each individual hydrocyclone.

Real time monitoring of each individual hydrocyclone would provide the ability to track the performance of individual hydrocyclones. This would enable the following:

The detection of hydrocyclones that require maintenance or have become plugged.

The detection of operational performance instabilities that cause extended periods of roping or surging.

The detection of chronic problems with certain hydrocyclones.

Tighter classification control with changing throughput demands and feed densities.

Increased up time or availability of the hydrocyclone battery.

Another common problem with hydrocyclone monitoring is reliably determining if a feed gate valve is open or closed. This is typically done using two micro switches. One switch indicates the valve is in the open position and the other switch indicates it is in the closed position. These switches are typically unreliable and require constant maintenance. A reliable maintenance free method is needed.

Moreover, FIG. 2 shows a classification stage generally indicated as 10 that may form part of a mineral extraction processing system, like the one shown in FIGS. 1A and 1B for extracting minerals from ore. The classification stage 10 includes a hydrocyclone battery 12 that receives a feed from a grinding stage, as shown in FIG. 1B. The hydrocyclone battery 12 is configured to respond to signaling from a signal processor or processor control module 14, and provide an effluent, e.g., a fine slurry or slurry feed, to a flotation stage shown in FIG. 1B. The classification stage 10 also may include a hydrocyclone split 16 that receives the slurry from the hydrocyclone battery 12, and also may receive signaling from the signal processor or processor control module 14, and may provide some portion of the slurry back to the mill stage shown in FIG. 1B, and may also provide another portion of the slurry as a flotation feed to a flotation stage shown in FIG. 1B consistent with that described in the aforementioned PCT application serial no. PCT/US09/43438. The signal processor or processor control module 14 may also send to or receive from one or more signals with a control room computer 50 (see FIG. 3A). The technique to track the flow performance of individual cyclones operating in parallel on a single battery is described in relation to the hydrocyclone battery 12 (i.e. the single battery), the signal processor or processor control module 14 and the cooperation of these two components.

FIG. 3A shows the hydrocyclone battery 12 (i.e. the single battery), the signal processor or processor control module 14 and the cooperation of these two components according to some embodiments of the present invention. For example, the hydrocyclone battery 12 may include a first and second hydrocyclone pair 12a, 12b. The first hydrocyclone pair 12a includes a first hydrocyclone 20 and a second hydrocyclone 30. The first hydrocyclone 20 has a cylindrical section 22 with an inlet portion 22a for receiving via a feed pipe 9 the feed from the grinding stage shown in FIG. 1B, an overflow pipe 24 for providing one portion of the fine slurry or slurry feed to either the flotation stage shown in FIG. 1B, or the hydrocyclone split 16 shown in FIG. 2, and has a conical base section 26 with underflow outlet 26a for providing a remaining portion of the fine slurry or slurry feed. See also FIG. 3B, which shows, by way of example, the cyclone 20 in enlarged detail.

Similarly, the second hydrocyclone 30 has a cylindrical section 32 with an inlet portion 32a for receiving the feed from the grinding stage shown in FIG. 1B, an overflow pipe 34 for providing one portion of the fine slurry or slurry feed to either the flotation stage shown in FIG. 1B, or the hydrocyclone split 16 shown in FIG. 2, and has a conical base section 36 with underflow outlet 36a for providing a remaining portion of the fine slurry or slurry feed.

As one skilled in the art would appreciate, the first and second hydrocyclones 20, 30 classify, separate and sort particles in the feed from the grinding stage based at least partly on a ratio of their centripetal force to fluid resistance. This ratio is high for dense and course particles, and low for light and fine particles. The inlet portion 22a, 32a receives tangentially the feed from the grinding stage shown in FIG. 1B, and the angle and the length of the conical base section 26, 36 play a role in determining its operational characteristics, as one skilled in the art would also appreciate.

At least one sensor 28 may be mounted on the overflow pipe 24 that is configured to respond to sound propagating in the overflow pipe 24 of the cyclone 20, and to provide at least one signal containing information about sound propagating through the slurry flowing in the overflow pipe 24 of the cyclone 20. Similarly, at least one corresponding sensor 38 is mounted on the overflow pipe 34 that is configured to respond to sound propagating in the overflow pipe 34 of the cyclone 30, and to provide at least one corresponding signal containing information about sound propagating through the slurry flowing in the overflow pipe 34 of the cyclone 30. By way of example, the at least one sensors 28, 38 may take the form of a SONAR-based clamp-around flow meter, which is known in the art consistent with that described below. The SONAR-based clamp-around flow meters 28, 38 may be clamped in whole or in part around some portion of the overflow pipes 24, 34. For example, the at least one sensor or meter 28, 38 may be mounted on the top of the overflow pipes 24, 34, or the at least one sensor or meter 28, 38 may be mounted on the bottom of the overflow pipe 24, 34. Alternatively, a pair of at least one sensor or meter 28, 38 may be mounted on the overflow pipes 24, 34, e.g., with one sensor or meter mounted on the top of the overflow pipes 24, 34, and with another sensor or meter mounted on the bottom of the overflow pipe 24, 34.

By way of example, in operation the SONAR-based clamp-around flow meters 28, 38 may be configured to respond to a strain imparted by the slurry, e.g., made up of water and fine particles, flowing in the overflow pipes 24, 34 of the cyclones 20, 30, and provide the signals along signal paths or lines 28a, 38a containing information about sound propagating through the slurry flowing in the overflow pipes 24, 34 of the cyclones 20, 30.

The classification stage 10 may include a signal processor or processor control module 14 (FIG. 2), which is also shown in FIG. 3A, having at least one module configured to respond to the signals along the signal paths or lines 28a, 38a containing information about sound propagating through the slurry flowing in the overflow pipes 24, 34 of cyclones 20, 30 operating in parallel on the cyclone battery 12 (see also FIG. 2), and determine the performance of individual cyclones 20, 30 based at least partly on the information contained in the signals. The signal processor or processor control module 14 may also send to or receive from one or more signals along signal path or line 14a with the control room computer 50 (see FIG. 2). The signal processor or processor control module 14 may also be configured to respond to signaling containing information about a battery flow rate, battery pressure, feed density, and cyclone status as indicated by individual gate valve positions of respective cyclones, which are provided from the cyclone battery 12 (FIG. 2).

Furthermore, in order to implement the technology set forth in the aforementioned patent application Ser. No. 13/389,546, embodiments included at least one sensor or meter 28a, 28b, 28c, 28d mounted on other parts of the cyclone or cyclone battery, or other parts or pipes connected to the cyclone or cyclone battery, including the feed pipe 9, or the inlet portion 22a, 32a, or the cylindrical section 22, 32, or the conical base section 26, 36, or the underflow outlet 26a, 36a, or some combination thereof, as shown by way of example in FIG. 3B.

SUMMARY OF THE INVENTION

In its broadest sense, the present invention provides new and unique techniques, e.g., in the form of a method and/or an apparatus, to optimize the performance of individual cyclones operating in a battery of cyclones.

According to some embodiments of the present invention, the apparatus may comprise at least one signal processor or signal processing module configured at least to:
respond to signaling containing information about particle sizes of solids forming part of a slurry stream being fed with a common feed flow into a battery of cyclones; and
determine which combinations of cyclones in the battery produce overflow that has undesirable particle size characteristics using a statistical algorithm or technique, based upon the signaling received.

The apparatus may also include one or more of the following features:

The at least one signal processor or signal processing module may be configured to provide corresponding signaling containing information about which combinations of cyclones in the battery produce overflow that has undesirable particle size characteristics. By way of example, the corresponding signaling may include, or take the form of, control signaling to control the operation of the battery, e.g., including information about certain combinations of cyclones to avoid, or preferentially to use, to minimize the total amount of coarse material having the undesirable particle size characteristics produced by the battery.

The signaling may include individual cyclone signaling sampled periodically and stored in a data set that can include information about other operational parameters, e.g., including which cyclones are open at a given time, a feed density, or a feed flow rate.

The at least one signal processor or signal processing module may be configured to analyze the data set over a predetermined period of time to extract statistically valid information as to which cyclones, and which combinations of cyclones, produce overflow that has the undesirable particle size characteristics, e.g., including too large of a particle size.

The at least one signal processor or signal processing module may be configured to identify one or more individual cyclones that are underperforming, including for some physical reason attributable to any particular cyclone.

The at least one signal processor or signal processing module may be configured to analyze the data set to identify combinations of cyclones that produce overflow streams that have too coarse of a particle size, even though the individual cyclones may have no physical problems, including due to the fact that a physical pattern of the cyclones operating can affect the flow pattern in a distribution box that feeds individual cyclones.

The physical pattern of the cyclones may include either adjacent cyclones operating next to each other in the battery, or alternating cyclones operating in an alternating pattern in the battery.

The at least one signal processor or signal processing module may be configured to determine if a type of pattern of the cyclones in the battery affects a flow velocity in a distribution box that can lead to non-uniform velocities within the distribution box that produces a density and particle size distribution that is not the same to each cyclone in the pattern.

The statistical algorithm or technique may be based upon one or more of the following determinations:

determining an average total flow of coarse particles for each combination of operating cyclones;

determining the combinations most frequently used in the battery, or determining the combinations that produce the most total coarse material over a predetermined time interval.

The corresponding signaling may contain information as to which combinations of cyclones in the battery to avoid, or preferentially use, to minimize the total amount of coarse material produced by the battery, including where the information may be used by an operator to make such a determination.

The at least one signal processor or signal processing module may be configured to identify one or more individual cyclones that are underperforming, including for some physical reason attributable to any particular cyclone, based upon the combinations determined.

The signaling may be received from sensors mounted on overflow pipes of individual cyclones that monitor a characteristic of the slurry stream, e.g., including a percentage of solids at or above a certain particle size.

The percentage of solids at or above the certain particle size may include P80, or percent solids above 200 um, or a number of impacts of large particles above 12 mm.

The apparatus may include the battery of cyclones.

The battery of cyclones may be configured so that between about 60% to 90% of the cyclones are operated at one time, including where an operator can change the number of cyclones operating, and which cyclones are operating to adjust to process throughput, and to equalize wear on the individual cyclones from abrasive slurry.

The battery of cyclones may include pneumatic as well as hydrocyclones.

The apparatus may include the sensors.

The sensors may include SONAR-based clamp-around flow meters configured on the cyclones in the battery, e.g., on the overflow pipes.

Each SONAR-based clamp-around flow meter may be configured to respond to a respective slurry stream fed into a respective cyclone in the battery, and provide respective signaling containing information about respective particle sizes of respective solids forming part of the respective slurry stream.

According to some embodiments, the present invention may take the form of a method comprising steps for responding with at least one signal processor or signal processing module to signaling containing information about particle sizes of solids forming part of a slurry stream being fed with a common feed flow into a battery of cyclones; and determining with the at least one signal processor or signal processing module which combinations of cyclones in the battery produce overflow that has undesirable particle size characteristics using a statistical algorithm or technique, based upon the signaling received.

The signal processor or signal processor module may take the form of a signal processor and at least one memory including a computer program code, where the signal processor and at least one memory are configured to cause the apparatus to implement the functionality of the present invention, e.g., to respond to signaling received and to determine the combinations of cyclones in the battery that are underperforming.

According to some embodiment, the present invention may take the form of apparatus comprising means for responding to signaling containing information about particle sizes of solids forming part of a slurry stream being fed with a common feed flow into a battery of cyclones; and means for determining combinations of cyclones in the battery produce overflow that has undesirable particle size characteristics using a statistical algorithm or technique, based upon the signaling received, consistent with that set forth herein.

According to some embodiments of the present invention, the apparatus may also take the form of a computer-readable storage medium having computer-executable components for performing the steps of the aforementioned method. The computer-readable storage medium may also include one or more of the features set forth above.

According to some embodiments of the present invention, the apparatus may include, or forms part of, a classification stage in a mineral extraction process.

BRIEF DESCRIPTION OF THE DRAWING

The drawing includes FIGS. 1-5, which are not necessarily drawn to scale, as follows:

FIG. 1A is a block diagram of a mineral extraction processing system in the form of a copper concentrator that is known in the art.

FIG. 1B is a block diagram showing typical processing stages of a mineral extraction processing system that is known in the art.

FIG. 2 is a block diagram showing a classification stage that is known in the art.

FIG. 3A is a diagram showing a cyclone battery, sensors, a signal processor and a remote computer processor that is known in the art.

FIG. 3B is a diagram showing a cyclone having a sensor arranged on an overflow pipe that is known in the art.

FIG. 3C is a diagram showing an oversized detection system on a hydrocyclone overflow line that is known in the art.

FIG. 3D is a diagram showing a control room display of real-time cyclone information that is known in the art.

DETAILED DESCRIPTION OF BEST MODE OF THE INVENTION

Summary of Basic Invention

Figure 4:
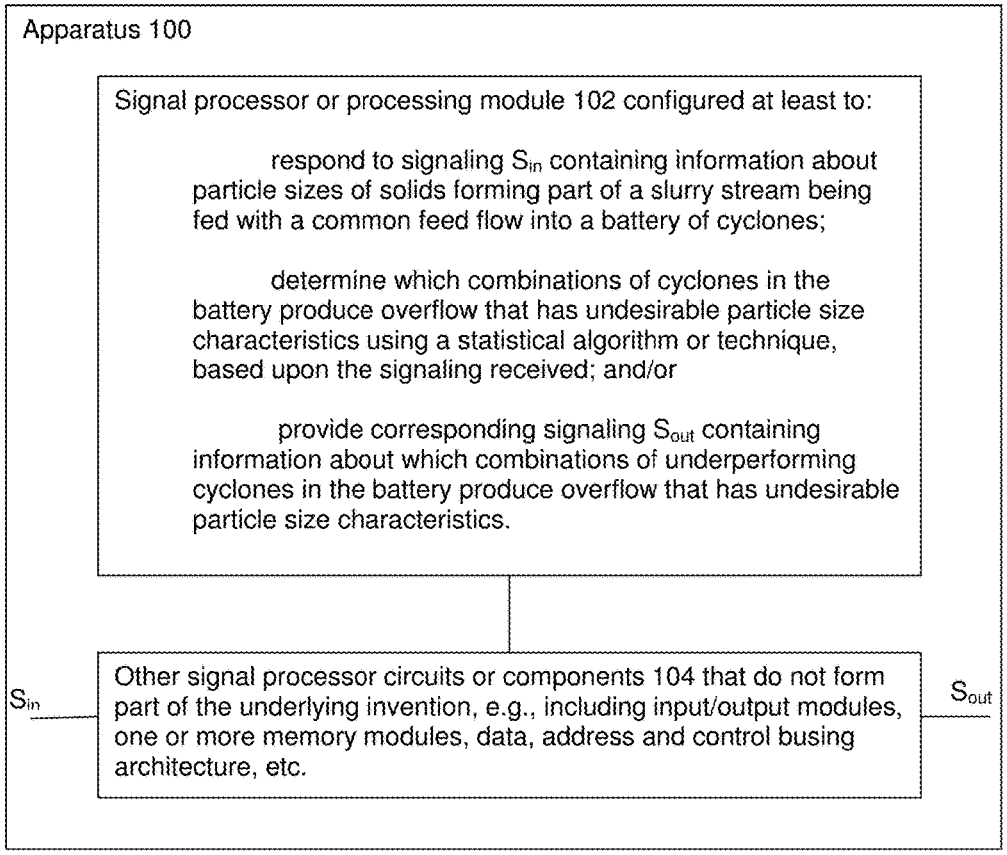
FIG. 4 shows a block diagram of apparatus, e.g., having a signal processor or signal processing module for implementing signal processing functionality according to some embodiments of the present invention.

In general, the present invention provides new and unique techniques to optimize the performance of individual cyclones operating in a battery of cyclones, e.g., like the hydrocyclone battery shown in FIGS. 2 and 3A.

In operation, sensing apparatus may be mounted on an overflow pipe of individual hydrocyclones that monitors a characteristic of the slurry stream such as percentage of solids at or above a certain particle size, e.g. P80, or percent solids above 200 um, or a number of impacts of large particles above 12 mm. The cyclones may be mounted and operated as a group, called a battery, and are fed by a common feed flow, consistent with that set forth herein. Typically, between 60% and 90% of the cyclones may be operated at one time, although the scope of the invention is not intended to be limited to any particular percentage of cyclones operated at one time. By way of example, operators may change the number of cyclones operating, and which cyclones are operating to adjust to process throughput, and to equalize wear on the individual cyclones from the abrasive slurry. Embodiments are also envisioned in which a controller controls, manages and/or changes the number of cyclones operating, and which cyclones are operating to adjust to process throughput, and to equalize wear on the individual cyclones from the abrasive slurry.

Individual cyclone signals may be sampled periodically and stored in a data set that can include other operational parameters such as which cyclones are open at a given time, a feed density, or a feed flow rate. By way of example, the periodic sampling may be implemented by using the sensor technology disclosed herein.

The data set may be analyzed over a sufficiently long time period to extract statistically valid information as to which cyclones, and which combinations of cyclones, produce overflow that has undesirable particle size characteristics, such as too large of a particle size. In this manner, individual cyclones can be identified that are performing badly, e.g., for some physical reason attributable to that cyclone. By way of example, the data set may be analyzed to make such an extraction by using the signal processing technology disclosed herein.

Additionally, and importantly with regard to the present invention, the data set may be analyzed to identify combinations of cyclones that produce overflow streams that have too coarse of a particle size, e.g., even though the individual cyclones may have no physical problems. By way of example, this is believed to be due to the fact that the physical pattern of the cyclones operating can affect the flow pattern, e.g., in a distribution box that feeds the individual cyclones, although the scope of the invention is not intended to be limited to any particular cause of such problems. For example, the physical pattern of the cyclones may include either the operating cyclones being adjacent to each other, or being formed or arranged in an alternating pattern. The type of pattern may affect the flow velocity in the distribution box that can lead to non-uniform velocities within the distribution box that produces a density and particle size distribution that is not the same to each cyclone. Again, by way of example, the data set may be analyzed to make such an identification by using the signal processing technology disclosed herein.

Examples of statistical techniques that may be applied may include: determining the average total flow of coarse particles for each combination of cyclones operating; determining the combinations most frequently used, or determining which combinations produce the most total coarse material over a reasonably long time interval. This information can provide operators with valuable information as to which combinations of cyclones to avoid, or preferentially use, to minimize the total amount of coarse material produced by the battery. By way of example, the data set may be analyzed to make such a statistical determination by using the signal processing technology disclosed herein to implement the associated signal processing functionality. The scope of the invention is not intended to limited to any particular time interval for making any such determination, e.g., which may include discrete predetermined time intervals having different lengths of time.

By way of example, the technique according to the present invention may be applied to pneumatic as well as hydrocyclones, including those either now known or later developed in the future.

FIG. 4

By way of example, FIG. 4 shows apparatus generally indicated as 100, e.g. having at least one signal processor or signal processing module 102 for implementing the signal processing functionality according to the present invention. In operation, the at least one signal processor or signal processing module 102 may be configured at least to:

respond to signaling $S_{in}$ containing information about particle sizes of solids forming part of a slurry stream being fed with a common feed flow into a battery of cyclones; and determine which combinations of cyclones in the battery produce overflow that has undesirable particle size characteristics using a statistical algorithm or technique, based upon the signaling received.

The signaling $S_{in}$ may be received from sensors mounted on overflow pipes of individual cyclones that monitor a characteristic of the slurry stream, including a percentage of solids at or above a certain particle size. The sensors may include, or take the form of, SONAR-based sensor, e.g., like the SONAR-based clamp-around flow meters 28, 38 configured on the overflow pipes 24, 34 of the cyclones 20, 30 in the battery 12 shown in FIGS. 3A, 3B. In operation, each such SONAR-based clamp-around flow meter may be configured to respond to a respective slurry stream fed into a respective cyclone in the battery, and provide respective signaling containing information about respective particle sizes of respective solids forming part of the respective slurry stream. A person skilled in the art would appreciate and understanding, e.g., after reading the instant patent application together with that known in the art, either how to implement suitable signaling processing functionality to provide such signaling containing such information using such a SONAR-based sensor, or how to adapt such a SONAR-based sensor to implement suitable signaling processing functionality to provide such signaling containing such information, without undue experimentation.

The at least one signal processor or signal processing module 102 may also be configured to determine which combinations of cyclones in the battery produce overflow that has undesirable particle size characteristics using the statistical algorithm or technique, e.g., that may include determining the average total flow of coarse particles for each combination of cyclones operating; determining the combinations most frequently used, and/or determining which combinations produce the most total coarse material over a long time interval. A person skilled in the art would appreciate and understanding, e.g., after reading the instant patent application together with that known in the art, how to implement suitable signaling suitable processing functionality to make one or more such determinations without undue experimentation.

The at least one signal processor or signal processing module 102 may be configured to provide corresponding signaling $S_{out}$ containing information about which combinations of cyclones in the battery produce overflow that has undesirable particle size characteristics. By way of example, the corresponding signaling $S_{out}$ may include, or take the form of, control signaling to control the operation of the battery, including certain combinations of cyclones to avoid, or preferentially to use, to minimize the total amount of coarse material having the undesirable particle size characteristics produced by the battery.

The apparatus 100 may also include, e.g., other signal processor circuits or components 104 that do not form part of the underlying invention, e.g., including input/output modules, one or more memory modules, data, address and control busing architecture, etc. In operation, the at least one signal processor or signal processing module 102 may cooperation and exchange suitable data, address and control signaling with the other signal processor circuits or components 104 in order to implement the signal processing functionality according to the present invention. By way of example, the signaling $S_{in}$ may be received by such an input module, provided along such a data bus and stored in such a memory module for later processing, e.g., by the at least one signal processor or signal processing module 102. After such later processing, processed signaling resulting from any such determination may be stored in such a memory module, provided from such a memory module along such a data bus to such an output module, then provided from such an output module as the corresponding signaling $S_{out}$, e.g., by the at least one signal processor or signal processing module 102.

According to some embodiments of the present invention, the apparatus 100 may also include, e.g., one or more sensors, the battery of cyclones, etc., e.g., consistent with that set forth herein.

The SONAR-based Clamp-around Flow Meters

SONAR-based clamp-around flow meters for sensing and providing signaling containing information about particle sizes of solids forming part of a slurry stream being fed with a common feed flow into a battery of cyclones are known in the art, and/or may be suitably adapted for sensing and providing such signaling, and the scope of the invention is not intended to be limited to any particular type or kind thereof either now known or later developed in the future. By way of example, such SONAR-based clamp-around flow meters, such as elements 28, 38 in FIG. 3A, are disclosed by way of example in whole or in part in U.S. Pat. Nos. 7,165,464; 7,134,320; 7,363,800; 7,367,240; and 7,343,820, all of which are incorporated by reference in their entirety. For example, SONAR-based clamp-around flow meters may take the form of a SONAR-based VF/GVF-100 meter, manufactured by the assignee of the present application. The scope of the invention is also intended to include other types or kinds of SONAR-based VF/GVF meters either now known or later developed in the future that perform the same basic functionality of the aforementioned SONAR-based VF/GVF meter as such functionality relates to implementing the present invention. The scope of the invention is also intended to include using the SONAR-based clamp-around flow meters alone or in combination with a density meter, e.g. for providing signaling containing information about the feed density, disclosed by way of example in whole or in part in U.S. Pat. Nos. 7,165,464; 7,134,320; 7,363,800; 7,367, 240; and 7,343,820.

The Signal Processor or Processor Control Module 100

The functionality of the signal processor or processor control module 100 may be implemented using hardware, software, firmware, or a combination thereof. In a typical software implementation, the processor module may include one or more microprocessor-based architectures having a microprocessor, a random access memory (RAM), a read only memory (ROM), input/output devices and control, data and address buses connecting the same, e.g., consistent with that shown in FIG. 4, e.g., see element 104. A person skilled in the art would be able to program such a microprocessor-based architecture(s) to perform and implement such signal processing functionality described herein without undue experimentation. The scope of the invention is not intended to be limited to any particular implementation using any such microprocessor-based architecture or technology either now known or later developed in the future.

The Cyclone or Hydrocyclone 20, 30

The cyclone or hydrocyclone, e.g., like elements 20, 30 in FIGS. 3A and 3B, are known in the art, and the scope of the invention is not intended to be limited to any particular type or kind thereof either now known or later developed in the future.

The Classification Stage 10

By way of example, the present invention as it relates to the classification stage 10 is described in relation to the mineral extraction processing system shown, e.g., in FIGS. 1A and 1B, which takes the form of a copper concentrator, although the scope of the invention is not intended to be limited to any particular type or kind of mineral process or mineral extraction processing system either now known or later developed in the future.

The classification stage 10 may also include one or more elements, devices, apparatus or equipment that are known in the art, do not form part of the underlying invention, and are not disclosed herein or described in detail for that reason.

The scope of the invention re classification stage and/or hydrocyclone applications is not intended to be limited to the type or kind of mineral being processed, or the type of mineral process, either now known or later developed in the future. By way of example, the scope of the invention is intended to include hydrocyclone applications include Molybdenum, Lead, Zinc, Iron, Gold, Silver, Nickel, Fluorite, Tantalum, Tungsten, Tin, Lithium, Coal, as well as, e.g. diamonds, etc.

FIG. 5

Figure 5:
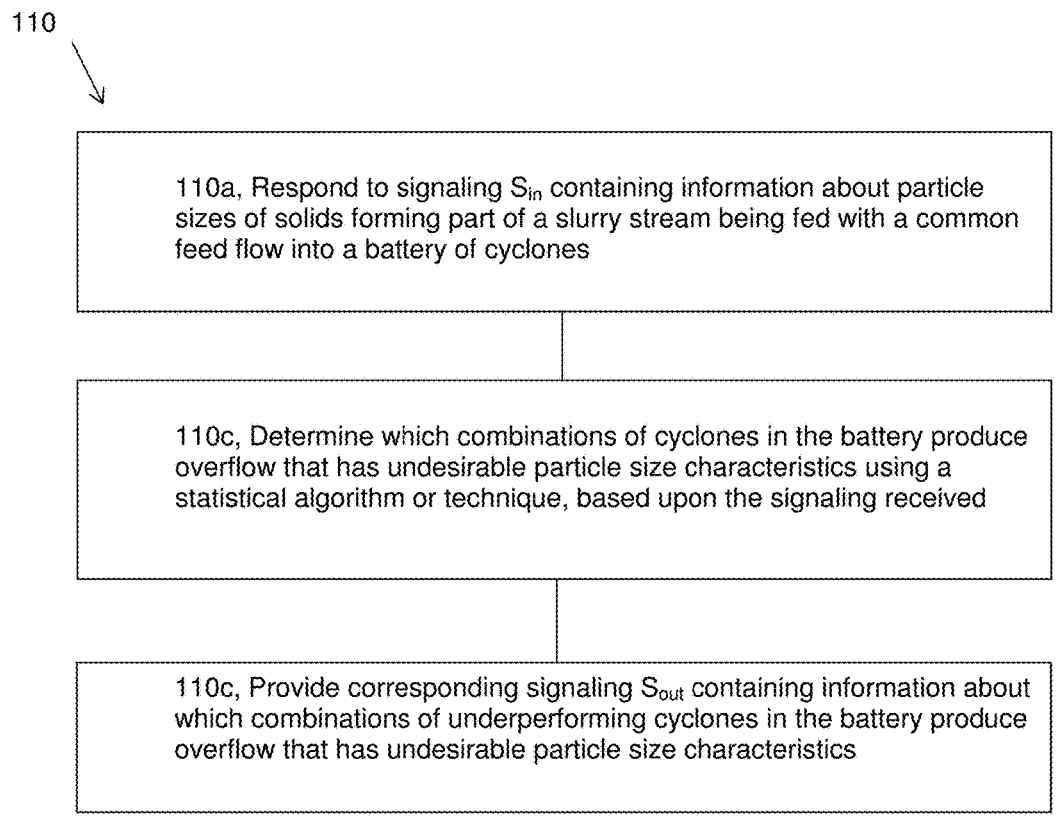
FIG. 5 shows a block diagram of a method, e.g., having steps for implementing the signal processing functionality according to some embodiments of the present invention.

FIG. 5 shows a method generally indicated as 110 having steps 110a, 110b and 110c for implementing the signal processing functionality, e.g., with at least one signal processor or signal processing module like element 102 in FIG. 4, according to some embodiments of the present invention.

The method 100 may include a step 110a for responding with at least one signal processor or signal processing module to signaling containing information about particle sizes of solids forming part of a slurry stream being fed with a common feed flow into a battery of cyclones; and a step 110b for determining with the at least one signal processor or signal processing module which combinations of cyclones in the battery produce overflow that has undesirable particle size characteristics using a statistical algorithm or technique, based upon the signaling received. The method 100 may also include a step 110c for providing corresponding signaling containing about which combinations of cyclones in the battery produce overflow that has undesirable particle size characteristics.

The method may also include one or more steps for implementing other features of the present invention set forth herein, including steps for making the various determinations associated with the statistical algorithm or technique set forth herein.

SONAR-Based Flow Monitoring

As one skilled in the art would appreciate, SONAR array-based flow measurement technology was introduced into the mineral processing industry over five years ago, and has since demonstrated significant usefulness and value in many difficult and critical flow monitoring applications. This robust non-invasive technology has become the standard for many companies in certain applications. The reader is referred to the aforementioned patent application Ser. No. 13/389,546 for a more comprehensive discussion of the same, e.g., including that set forth in relation to FIGS. 13-19 therein.

Applications Re Other Industrial Processes

By way of example, the present invention is described in relation to, and part of, a mineral extraction processing system for extracting minerals from ore. However, the scope of the invention is intended to include other types or kinds of industrial processes either now known or later developed in the future, including any mineral process, such as those related to processing substances or compounds that result from inorganic processes of nature and/or that are mined from the ground, as well as including either other extraction processing systems or other industrial processes, where the sorting, or classification, of product by size is critical to overall industrial process performance.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
a battery of cyclones configured to process a slurry stream being fed with a common feed flow:
sensors being mounted on the battery of cyclones, each sensor configured to sense particle sizes of solids forming part of a slurry stream overflow, and provide signaling containing information about the particle sizes of solids forming part of the slurry stream overflow;
at least one signal processor or signal processing module configured at least to:
respond to the signaling; and
provide corresponding signaling to control the operation of the battery by determining which combinations of cyclones in the battery produce the slurry stream overflow that has undesirable particle size characteristics using a statistical algorithm or technique, based upon the signaling received.

2. Apparatus according to claim 1, wherein the signaling includes individual cyclone signaling sampled periodically and stored in a data set that can include information about other operational parameters, including which cyclones are open at a given time, a feed density, or a feed flow rate.

3. Apparatus according to claim 2, wherein the at least one signal processor or signal processing module is configured to analyze the data set over a predetermined period of time to extract statistically valid information as to which cyclones, and which combinations of cyclones, produce overflow that has the undesirable particle size characteristics, including too large of a particle size.

4. Apparatus according to claim 3, wherein the at least one signal processor or signal processing module is configured to identify one or more individual cyclones that are underperforming, including for some physical reason attributable to any particular cyclone.

5. Apparatus according to claim 3, wherein the at least one signal processor or signal processing module is configured to analyze the data set to identify combinations of cyclones that produce overflow streams that have too coarse of a particle size, even though the individual cyclones may have no physical problems, including due to the fact that a physical pattern of the cyclones operating can affect the flow pattern in a distribution box that feeds individual cyclones.

6. Apparatus according to claim 5, wherein the physical pattern of the cyclones includes either adjacent cyclones operating next to each other in the battery, or alternating cyclones operating in an alternating pattern in the battery.

7. Apparatus according to claim 5, wherein the at least one signal processor or signal processing module is configured to determine if a type of pattern of the cyclones in the battery affects a flow velocity in the distribution box that can lead to non-uniform velocities within the distribution box that produces a density and particle size distribution that is not the same to each cyclone in the pattern.

8. Apparatus according to claim 1, wherein the statistical algorithm or technique is based upon one or more of the following determinations:
determining an average total flow of coarse particles for each combination of operating cyclones;
determining the combinations most frequently used in the battery, or
determining the combinations that produce the most total coarse material over a predetermined time interval.

9. Apparatus according to claim 1, wherein the corresponding signaling contains information as to which combinations of cyclones in the battery to avoid, or preferentially use, to minimize the total amount of coarse material produced by the battery, including where the information may be used by an operator to make such a determination.

10. Apparatus according to claim 1, wherein the at least one signal processor or signal processing module is configured to identify one or more individual cyclones that are underperforming, including for some physical reason attributable to any particular cyclone, based upon the combinations determined.

11. Apparatus according to claim 1, wherein the sensors are mounted on overflow pipes of individual cyclones that monitor a characteristic of the slurry stream overflow, including a percentage of solids at or above a certain particle size.

12. Apparatus according to claim 11, wherein the percentage of solids at or above the certain particle size includes P80, or percent solids above 200 um, or a number of impacts of large particles above 12 mm.

13. Apparatus according to claim 1, wherein the battery of cyclones is configured so that between about 60% to 90% of the cyclones are operated at one time, including where an operator can change the number of cyclones operating, and which cyclones are operating to adjust to process throughput, and to equalize wear on the individual cyclones from abrasive slurry.

14. Apparatus according to claim 1, wherein the battery of cyclones comprises pneumatic as well as hydrocyclones.

15. Apparatus according to claim 11, wherein the sensors comprise SONAR-based clamp-around flow meters configured on the cyclones in the battery.

16. Apparatus according to claim 15, wherein each SONAR-based clamp-around flow meter is configured to respond to a respective slurry stream fed into a respective cyclone in the battery, and provide respective signaling containing information about respective particle sizes of respective solids forming part of the respective slurry stream.

17. A method comprising:
configuring a battery of cyclones to process a slurry stream being fed with a common feed flow;
mounting sensors on the battery of cyclones to sense particle sizes of solids forming part of a slurry stream overflow and provide signaling containing information about the particle sizes of solids forming part of the slurry stream overflow;
responding with at least one signal processor or signal processing module to the signaling; and
providing corresponding signaling to control the operation of the battery by determining with the at least one signal processor or signal processing module which combinations of cyclones in the battery produce the slurry stream overflow that has undesirable particle size characteristics using a statistical algorithm or technique, based upon the signaling received.

18. A method according to claim 17, wherein the signaling includes individual cyclone signaling sampled periodically and stored in a data set that can include information about other operational parameters, including which cyclones are open at a given time, a feed density, or a feed flow rate.

19. A method according to claim 18, wherein the method comprises analyzing with the at least one signal processor or signal processing module the data set over a predetermined period of time to extract statistically valid information as to which cyclones, and which combinations of cyclones, produce overflow that has the undesirable particle size characteristics, including too large of a particle size.

20. A method according to claim 19, wherein the method comprises identifying with the at least one signal processor or signal processing module one or more individual cyclones that are underperforming, including for some physical reason attributable to any particular cyclone.

21. A method according to claim 19, wherein the method comprises analyzing with the at least one signal processor or signal processing module the data set to identify combinations of cyclones that produce overflow streams that have too coarse of a particle size, even though the individual cyclones may have no physical problems, including due to the fact that a physical pattern of the cyclones operating can affect the flow pattern in a distribution box that feeds individual cyclones.

22. A method according to claim 21, wherein the physical pattern of the cyclones includes either adjacent cyclones operating next to each other in the battery, or alternating cyclones operating in an alternating pattern in the battery.

23. A method according to claim 21, wherein the method comprises determining with the at least one signal processor or signal processing module if a type of pattern of the cyclones in the battery affects a flow velocity in the distribution box that can lead to non-uniform velocities within the distribution box that produces a density and particle size distribution that is not the same to each cyclone in the pattern.

24. A method according to claim 17, wherein the statistical algorithm or technique is based upon making with the at least one signal processor or signal processing module one or more of the following determinations:
determining an average total flow of coarse particles for each combination of operating cyclones;
determining the combinations most frequently used in the battery, or
determining the combinations that produce the most total coarse material over a predetermined time interval.

25. A method according to claim 17, wherein the corresponding signaling contains information as to which combinations of cyclones in the battery to avoid, or preferentially use, to minimize the total amount of coarse material produced by the battery, including where the information may be used by an operator to make such a determination.

26. A method according to claim 17, wherein the method comprises identifying with the at least one signal processor or signal processing module one or more individual cyclones that are underperforming, including for some physical reason attributable to any particular cyclone, based upon the combinations determined.

27. A method according to claim 17, wherein the method comprises mounting the sensors on overflow pipes of individual cyclones that monitor a characteristic of the slurry stream overflow, including a percentage of solids at or above a certain particle size.

28. A method according to claim 27, wherein the percentage of solids at or above the certain particle size includes P80, or percent solids above 200 um, or a number of impacts of large particles above 12 mm.

29. A method according to claim 17, wherein the method comprises configuring the battery of cyclones so that between about 60% to 90% of the cyclones are operated at one time, including where an operator can change the number of cyclones operating, and which cyclones are operating to adjust to process throughput, and to equalize wear on the individual cyclones from abrasive slurry.

30. A method according to claim 21, wherein the battery of cyclones comprises pneumatic as well as hydrocyclones.

31. A method according to claim 27, wherein the method comp rises configuring the sensors as SONAR-based clamp-around flow meters arranged on the cyclones in the battery.

32. A method according to claim 31, wherein the method comprises configuring each SONAR-based clamp-around flow meter to respond to a respective slurry stream fed into a respective cyclone in the battery, and provide respective signaling containing information about respective particle sizes of respective solids forming part of the respective slurry stream.

33. Apparatus, including a computer-readable storage medium having computer-executable components, configured to perform the steps of the method recited in claim 17.

34. Apparatus according to claim 1, wherein the apparatus comprises, or forms part of, a classification stage in a mineral extraction process.

35. Apparatus according to claim 15, wherein each SONAR-based clamp-around flow meter is configured to respond to a respective slurry stream overflow fed from a respective cyclone in the battery, and provide respective signaling containing information about respective particle sizes of respective solids forming part of the respective slurry stream overflow.

36. A method according to claim 31, wherein the method comprises configuring each SONAR-based clamp-around flow meter to respond to a respective slurry stream fed into a respective cyclone in the battery, and provide respective signaling containing information about respective particle sizes of respective solids forming part of the respective slurry stream.

* * * * *